United States Patent [19]

Herold et al.

[11] Patent Number: 4,538,070
[45] Date of Patent: Aug. 27, 1985

[54] APPARATUS FOR TREATING DENTAL PROSTHETIC PARTS WITH RADIATION

[75] Inventors: Wolf-Dietrich Herold, Hechendorf; Karl L. Grafwallner, Munich; Michael Keller, Lochham, all of Fed. Rep. of Germany

[73] Assignee: ESPE Fabrik pharmazeutischer Praeparate GmbH, Fed. Rep. of Germany

[21] Appl. No.: 500,849

[22] Filed: Jun. 3, 1983

[30] Foreign Application Priority Data

Jul. 8, 1982 [DE] Fed. Rep. of Germany ....... 3225589

[51] Int. Cl.$^3$ .............................................. C08J 3/28
[52] U.S. Cl. ............................. 250/504 R; 250/492.1; 250/455.1
[58] Field of Search ............ 250/492.1, 504 R, 504 H, 250/453.1, 454.1, 455.1

[56] References Cited

U.S. PATENT DOCUMENTS 3,906,236  9/1975  Callahan ............................ 250/455.1
4,221,994  9/1980  Friedman et al. .......... 250/504 H X
4,421,987  12/1983  Herold ............................. 250/492.1

Primary Examiner—Alfred E. Smith
Assistant Examiner—Jack I. Berman
Attorney, Agent, or Firm—Barnes & Thornburg

[57] ABSTRACT

An apparatus for treating dental prosthetic parts includes a lamp, a reflector, a filter and an optical wave guide to project radiation of a selected spectral range onto a location of treatment. When an object is placed at this location, it actuates an infrared proximity switch which turns on the lamp for at least a predetermined period of time. A protective pane is disposed in front of the lamp and location of treatment which absorbs the selected spectral range but transmits other visible light to avoid glaring of an operator. The portion of the apparatus beneath the location of treatment includes a plate which is also absorptive in the selected spectral range to avoid disturbing reflections, and is replaceable since it may become contaminated by dental material dropping onto it and curing there.

12 Claims, 4 Drawing Figures

APPARATUS FOR TREATING DENTAL PROSTHETIC PARTS WITH RADIATION

DESCRIPTION

The invention relates to an apparatus for treating dental prosthetic parts and materials with radiation of a selected spectral range.

In the dental technical field, materials that are polymerizable by light with the aid of a photoinitiator system and curable are used for example for the production of dental prosthetic parts, such as crowns, individual teeth, bridges, dentures or parts thereof.

For initiating the polymerization irradiation, devices using halogen quartz lamps as light sources have been developed. Such an irradiation apparatus is described for example in German Laying Open Print No. 2 901 534. The apparatus described there is a hand-held device having a pistol-like handle and a manual switch to actuate the light source.

The practical use of this apparatus for the production of crowns and bridges involves drawbacks as described in the following. To produce a dental prosthetic part, such as a crown, the operator will apply a thin coating of a photopolymerizable material, for example on a metal part. The material is applied by means of a thin brush and then irradiated by means of the irradiation apparatus, so that polymerization is started. This operation consisting in the application and subsequent irradiation is repeated several times, until the layers applied one upon the other have taken the desired external shape of the dental object. For each irradiation operation, the operator is requested to put aside his tool, take up the irradiation apparatus and effect the irradiation.

This required tool-changing proves to be unpractical and prolongs the period of time required for carrying out the necessary operations. Stationary apparatus as for treating and irradiating dental prosthetic parts, such as known from European patent application publication No. 37 461 do not relieve this difficulty because, in such apparatuses, the dental objects have to be placed into a particular receptacle and the apparatus has to be switched on by hand.

It is an object of the present invention to provide an apparatus for treating dental prosthetic parts and materials with radiation, which avoids the problems encountered with prior art apparatuses as described above. More specifically, it is an object to provide such an apparatus which is easier to operate and renders the dentist's or dental technician's work simpler and less time-consuming.

In view of this object, an apparatus for treating dental prosthetic parts and material with radiation of a selected spectral range includes a source of radiation which comprises said selected spectral range, reflecting means for directing radiation of said selected spectral range onto a location of treatment, filter means substantially transmitting said selected spectral range, disposed between said source and said location of treatments, and a proximity switch for switching on said source, the switch being actuated by the presence of an object at said location of treatment.

Thus, the irradiation apparatus of the invention is provided with a proximity switch which is actuated when the dental prosthetic part to be irradiated is moved to the location of treatment. The operator may therefore continue to hold the tools needed for working at the dental prosthetic part in his hand while performing the irradiation.

The proximity switch may be a device having a capacity and/or inductance bridge which responds to the change of an electrostatic or electromagnetic field, for example a high frequency field, on approach of an object. In a preferred embodiment of the invention the proximity switch consists of an infrared light source and an infrared detector. When an object approaches the proximity switch infrared light is reflected into the infrared detector, so that the switch is actuated.

According to a preferred embodiment of the invention, the proximity switch is coupled with a timer circuit which, when actuated, switches on the lamp for a predetermined minimum operation period. As is known with halogen-quartz lamps, the halogen circulation, by which the service life of such a lamp is prolonged, is established only above certain operation time on. If an object were held under the irradiation apparatus for a short time only, the lamp would, in case of a direct control, be switched on by the proximity switch for a short period only, thus possibly shorter than the prescribed minimum period of operation, and the service file would be considerably shortened in case of repeated operations of such a short duration. By the provision of the timer circuit, the minimum operation period is always maintained.

In another embodiment, the lamp is preheated with a voltage below the standard voltage as soon as the apparatus is connected to the main voltage. This decisively increases the number of operation cycles and prolongs the service life of the lamp.

The wave length of the selected light is in the ultraviolet and visible ranges, preferably between 400 and 500 nm and particularly in the range of about 460 nm.

A light guide is provided for achieving uniform brightness intensity over a given irradiation area. The beam of radiation is preferably restricted to a diameter of about 10 mm in order to achieve a sufficient intensity at a sufficiently large area of illumination.

The lamp and its exit opening are preferably so arranged that the emitted beam extends in a downwardly declining direction. A plate absorbing the respective spectral range is provided below the location of treatment to prevent any light that may disturb the operator's work from being reflected from the table on which the apparatus stands or from the foot of the apparatus itself. This plate is preferably replaceable, so that dental material dropping down during operation and curing in the course of time by the radiation may be removed without any problems.

A protective pane may be provided near the beam exit opening to absorb the selected spectral range while essentially transmitting the other visible light. The operator may thus observe the dental object through the protective pane without being dazzled by the light.

To facilitate the work, the apparatus is designed with a box-type housing rearwardly inclined with respect to the vertical. The upper part of the housing has a forwardly protruding position in which the lamp and the beam exit are disposed. The inclined housing accomodates the current supply and the timer circuit for the lamp.

A preferred embodiment of the invention will be described with reference to the drawings, in which.

Figure 1:
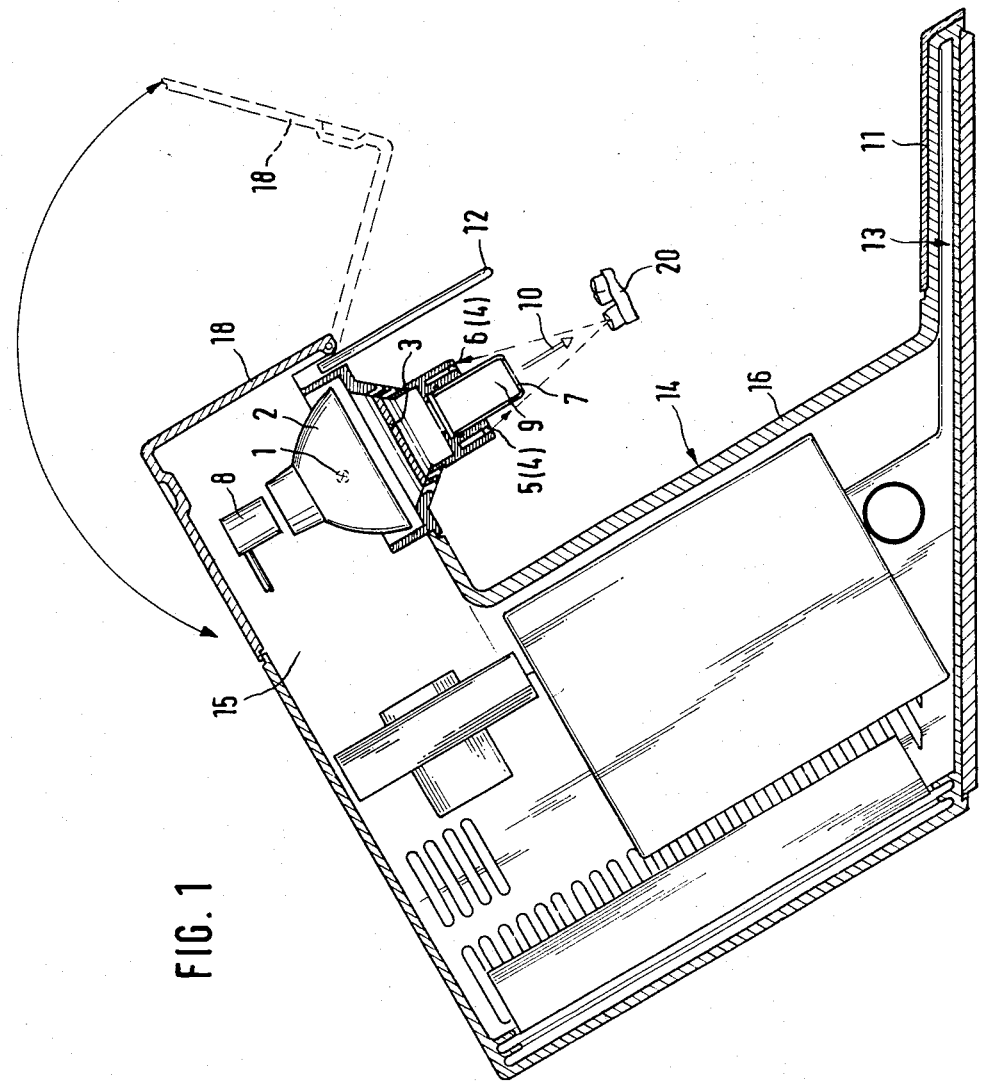
FIG. 1 is a schematic section through an apparatus according to the invention.

As shown in FIG. 1, the apparatus includes a foot 13 and a box-shaped housing 14 which is inclined rearwardly with respect to the vertical. At the upper part of the housing 14, an extension 15 is provided in which a lamp 1 with a reflector 2 is accomodated in a socket 8. In the path of light from the reflector 2, a filter arrangement 3 is disposed which transmits the selected spectral range initiating the photopolymerization of the dental material nearly unobstructed while absorbing other light, such as infrared radiation. A light guide 9 is arranged below the filter to collimate the emitted light 10. The beam exit opening 7 of the light guide has a diameter of about 10 mm.

A proximity switch 4 includes an infrared source 5 from which infrared light is emitted. When a dental prosthetic part 20 approaches the irradiation apparatus, it will reflect the infrared light towards a sensor 6. The output signal of the detector 6 actuates a switch not shown in FIG. 2, which turns on the lamp 1.

A protective pane 12 is provided for protecting the operator. This protective pane absorbs light of the selected range while transmitting to a certain extent the other visible light, so that the dental prosthetic part 20 held under the beam exit opening 7 can be observed without glaring.

The lamp and reflector are so disposed that the light 10 is emitted approximately parallel to front side 16 of housing 14.

The extension 15, in which the light source is provided, can be opened by a hinged part 18, so that the lamp 1 can be easily replaced.

Below the beam exit opening and in particular below the place where dental prosthetic part 20 is held in the emitted light, a light-absorbing plate 11 is disposed which prevents light from being reflected to the eyes of the operator. The plate 11 is replaceable and may be easily exchanged in case it is contaminated by dental material dropping down on it.

Figure 2:
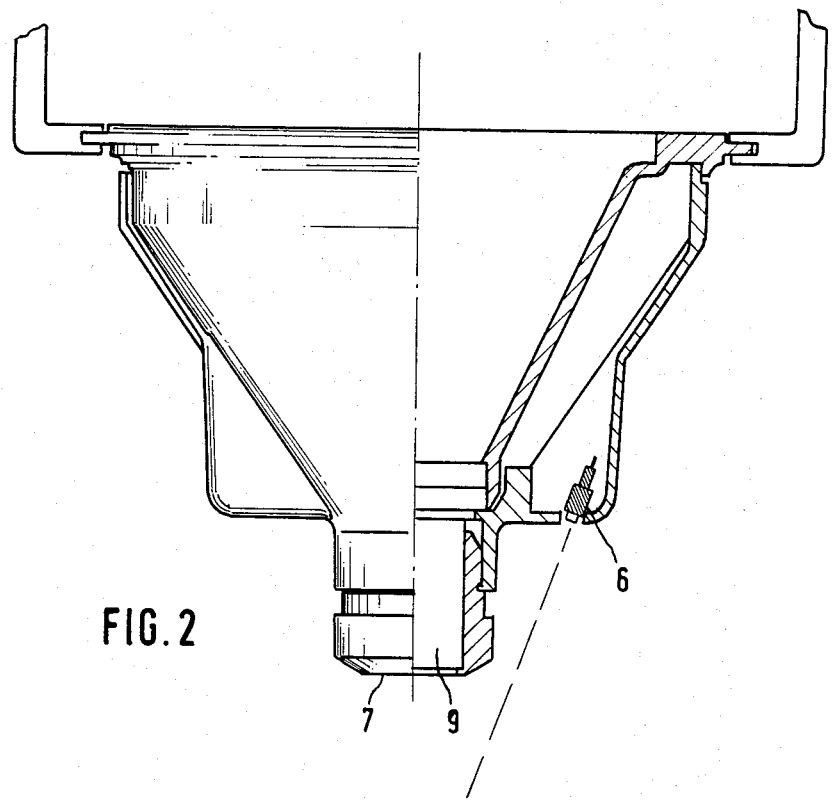
FIG. 2 is partly a side view and partly a section through the light emitting part of the apparatus.

As shown in somewhat greater detail in FIG. 2, a detector 6, which is a component of the proximity switch 4, is disposed so as to receive the light emitted from the infrared light source 5 and reflected by the irradiation object only if the latter is placed at a given distance from the beam exit opening 7.

Figure 3:
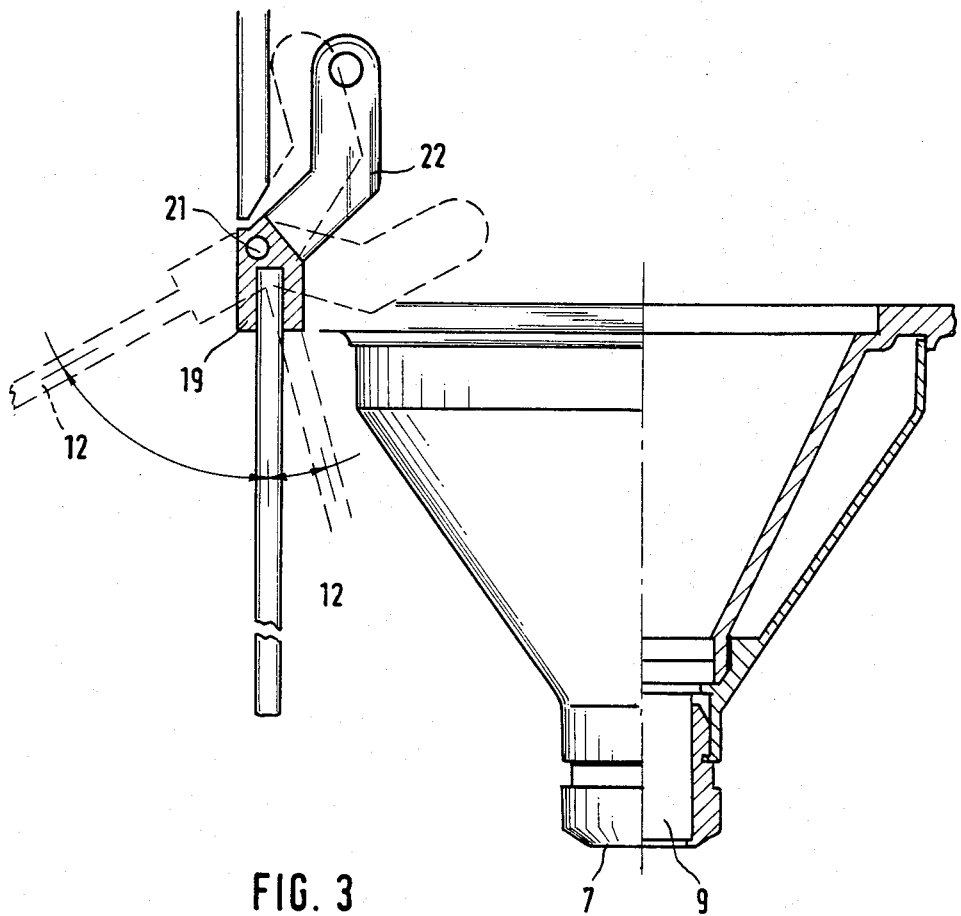
FIG. 3 illustrates the mounting of a protective pane.

FIG. 3 shows the pivotable mounting of the protective pane 12 on the housing. The protective panel 12 is held by a fork 19 which pivots about an axis 21. A bent lever 22 permits the protective pane 12 to be locked in various positions.

Figure 4:
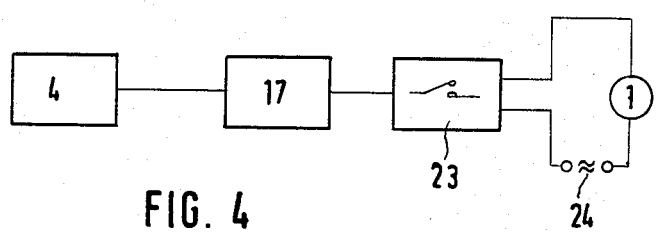
FIG. 4 is a block diagram for a circuit for operating the lamp.

According to the block diagram of FIG. 4, the proximity switch 4 supplies an output signal to a timer circuit 17 if an object is placed at the location of treatment below the light exit opening of the irradiation apparatus. This timer circuit 17 actuates an on/off switch 23 through which a voltage source 24 is connected to the lamp 1. The timer circuit is designed to actuate the switch immediately upon receipt of the output signal from the proximity switch 4, so that the lamp 1 is immediately turned on. When the object is removed, the output signal of proximity switch 4 ceases. If this occurs within a given minimum period of time, the output signal of timer circuit 17 remains on and continues to keep switch 23 in its actuated state. On the other hand, if the signal from the proximity switch 4 terminates after expiry of this minimum period of time, the output signal of the timer circuit will also cease and turn off the switch 23 simultaneously. A certain minimum operating period of the light source 1 is thus ensured.

We claim:

1. An apparatus for treating dental prosthetic parts and materials with radiation of a selected spectral range, including
a source of radiation which comprises said selected spectral range,
reflecting means for directing radiation of said selected spectral range onto a location of treatment,
filter means substantially transmitting said selected spectral range, disposed between said source and said location of treatment, and
a non-contacting proximity switch for switching on said source, the switch being actuated by the presence of an object at said location of treatment.

2. The apparatus of claim 1, wherein said proximity switch includes an infrared light source and an infrared detector.

3. The apparatus of claim 1, wherein said proximity switch includes capacity measuring means.

4. The apparatus of claim 1, wherein said proximity switch includes inductance measuring means.

5. The apparatus of claim 1, further including a timer circuit for switching on said source of radiation for a predetermined minimum period of time upon actuation by said proximity switch.

6. The apparatus of claim 5, including means for preheating said source of radiation when the apparatus is in its operating condition.

7. The apparatus of claim 1, further including an optical wave guide for collimating the emitted radiation and guiding it towards said location of treatment.

8. The apparatus of claim 7, wherein the radiation emitted from said wave guide has a beam diameter of less than about 10 mm.

9. The apparatus of claim 1, wherein said emitted beam extends in a downwardly declining direction towards a foot portion of the apparatus, this foot portion including means absorbing said selected spectral range.

10. The apparatus of claim 9, wherein said absorbing means includes a plate replaceably mounted on said foot portion.

11. The apparatus of claim 1, further including protective means disposed between the location where said radiation exits from the arrangement including said source, reflecting and filter means, and the eyes of an operator, said protective means being strongly absorptive in said selected spectral range while essentially transparent to the other visible light.

12. The apparatus of claim 11, wherein said protective means includes a pane swingably hinged to the apparatus.

* * * * *